US 6,551,625 B1

(12) United States Patent
Hilaire et al.

(10) Patent No.: US 6,551,625 B1
(45) Date of Patent: Apr. 22, 2003

(54) INHIBITING DISAGREEABLE ODORS WITH EXTRACTS OF UNDIFFERENTIATED PLANT CELLS

(75) Inventors: Pascal Hilaire, Vouvray (FR); Richard Martin, Rochecorbon (FR); Christophe Courbiere, Paris (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 09/609,321

(22) Filed: Jun. 30, 2000

(30) Foreign Application Priority Data

Jul. 2, 1999 (FR) .............................. 99 08569

(51) Int. Cl.[7] .......................... A61K 35/78; A61K 7/00; A61K 7/06; C12N 5/00; A01N 25/00
(52) U.S. Cl. ..................... 424/725; 424/47; 424/70; 424/74; 424/746; 435/419; 435/430; 435/431; 514/844
(58) Field of Search ............... 424/47, 74, 70, 424/195.1, 746; 435/172.3, 419, 430, 431; 514/844; 800/295

(56) References Cited

U.S. PATENT DOCUMENTS 5,380,521 A * 1/1995 Saihara et al.
6,060,061 A * 5/2000 Breton et al. ............ 424/195.1

FOREIGN PATENT DOCUMENTS

| EP | 0765668 | 4/1997 |
| FR | 2731162 | 9/1996 |
| FR | 2744915 | 8/1997 |
| FR | WO 98/04276 | * 2/1998 |
| FR | 2777191 | 10/1999 |
| JP | 407171209 A | * 7/1995 |

OTHER PUBLICATIONS

Smithosonoian Institute 1996 ING Database (rathbun.si.edu/botany) Jasminum Linnaeus.*

* cited by examiner

Primary Examiner—Christopher R. Tate
Assistant Examiner—Kailash C. Srivastava
(74) Attorney, Agent, or Firm—Burns, Doane, Swecker & Mathis, L.L.P.

(57) ABSTRACT

Disagreeable/objectionable odors, notably body and sweat odors, are inhibited by treating the situs of same, for example the skin, hair and/or mucous membranes of a human subject, with hygienic/deodorant compositions comprising effective odor-/body odor-inhibiting amounts of at least one extract of undifferentiated plant cells.

15 Claims, No Drawings

INHIBITING DISAGREEABLE ODORS WITH EXTRACTS OF UNDIFFERENTIATED PLANT CELLS

CROSS-REFERENCE TO PRIORITY APPLICATION

This application claims priority under 35 U.S.C. §119 of FR-99/08569, filed Jul. 2, 1999, hereby expressly incorporated by reference.

BACKGROUND OF THE INVENTION

1. Technical Field of the Invention

The present inventions relates to novel hygienic/deodorant compositions comprising at least one extract of undifferentiated plant cells with the exception of cells from the genus Bellis, for inhibiting disagreeable or objectionable odors, especially body odors, and to the use of such novel compositions for the cosmetic applications indicated above.

2. Description of the Prior Art

The anatomy and physiology of human and animal skin vary from one part of the body to another. However, irrespective of the anatomical region, the skin contains sebaceous glands and sweat glands whose excretions contain, inter alia, water, amino acids, urea, electrolytes and/or specific fatty acids. Other than the fact that these excretions represent excellent nutrient media for the development of, principally bacterial, flora which colonizes the skin, their individual components, once in contact with the air, undergo chemical reactions, for example such as oxidation, which degrade them and promote formation of products responsible for body odors which occasionally may prove to be embarrassing.

Certain substances which are natural odor inhibitors (bactericidal and/or bacteriostatic) due to the partial degradation of the complex lipids secreted by the sweat glands are volatile and may be associated with a strong odor which it is customary to combat.

However, skin excretions are not the only factors responsible for body odor. The skin flora are themselves partly responsible therefor.

In cosmetics, it is well known to formulate deodorant products for topical application, these products containing active agents such as antiperspirants or bactericides to reduce or even prevent a generally unpleasant body odor.

Antiperspirant substances elicit the effect of limiting the flow of sweat. They are generally aluminum salts, which are firstly irritant to the skin and secondly reduce the flow of sweat by modifying the skin physiology, which is unsatisfactory.

By inhibiting the growth of the. skin flora responsible for body odor, bactericidal substrates present the drawback of not being active against the sweat odor already developed. These bactericidal products, of which the one most commonly used is triclosan (5-chloro-2-(2,4-dichlorophenoxy) phenol), are thus insufficiently effective over the long term.

Further, deodorants can modify the microflora, mainly towards Gram-negative bacteria, and consequently trigger infections.

Thus, serious need continues to exist for effective compounds and/or compositions for treating disagreeable/objectionable body odors which present no adverse side effects.

SUMMARY OF THE INVENTION

It has now surprisingly and unexpectedly been determined that extracts of undifferentiated plant cells can inhibit disagreeable/objectionable odors, particularly the odors associated with human sweat.

Briefly, thus, the present invention features novel hygienic/deodorant compositions comprising at least one extract of undifferentiated plant cells, with the exception of cells from the genus Bellis, such novel compositions being well suited for inhibiting odors.

According to the this invention, at least one extract of undifferentiated plant cells is employed to inhibit body odors and, even more especially, the odors due to animal or human sweat.

This invention preferably deodorizes human sweat.

DETAILED DESCRIPTION OF BEST MODE AND SPECIFIC/PREFERRED EMBODIMENTS OF THE INVENTION

More particularly according to the present invention, by the expression "undifferentiated plant cells" is intended any plant cell which has none of the characteristics of a particular specialization and which is capable of living by itself and independently of other cells.

Undifferentiated plant cells can be obtained from plant material derived from the whole plant or from a plant part such as the leaves, stalks, flowers, petals, roots, fruit, seed or anthers.

The undifferentiated plant cells are preferably obtained from leaves.

The undifferentiated plant cells which are employed according to the invention can be obtained from plants obtained by in vivo culturing or derived from in vitro culturing.

By the expression "in vivo culturing" is intended any culturing of conventional type, i.e., in soil in the open air or in a greenhouse, or, alternatively, without soil.

By the expression "in vitro culturing" is intended the set of techniques known to those skilled in the art which makes it possible to artificially obtain a plant or a part of a plant. The pressure of selection imposed by the physicochemical conditions during the growth of plant cells in vitro makes it possible to obtain a standardized plant material which is available throughout the year, unlike plants cultivated in vivo.

Undifferentiated plant cells obtained via in vitro culturing are preferably employed according to the invention.

The undifferentiated plant cells according to the invention may be obtained by any method known in the prior art. In this respect, exemplary are the methods described by E. F. George and P. D. Sherrington in *Plant Propagation by Tissue Culture,* handbook and directory of commercial laboratories (Exegetics Ltd. 1984).

The culture media which can be used according to the invention are those generally known to those skilled in the art. Examples are the Gamborg, Murashige-Skoog, Heller, White, etc. media. Complete descriptions of these media are contained in "Plant Culture Media: formulations and uses" by E. F. George, D. J. M. Puttock and H. J. George (Exegetics Ltd. 1987, volumes 1 & 2).

The undifferentiated plant cells are preferably prepared by culturing on Murashige-Skoog medium.

Any extraction technique known to those skilled in the art can be used to prepare the extract according to the invention.

Thus, the extracts according to the invention may be in any known form. Particularly exemplary are aqueous, alcoholic, in particular ethanolic, or aqueous/alcoholic extracts.

According to the invention, the extract is preferably an aqueous extract.

It is also envisaged to employ an extract prepared via the technique described in FR-95/02379, assigned to the assignee hereof.

Thus, in a first step, the plant material is ground in an aqueous solution under cold conditions, and in a second step the particles in suspension are removed from the aqueous solution derived from the first step. This aqueous solution corresponds to the extract.

The aqueous solution derived from the second step is optionally sterilized in a third step.

The extract can advantageously be lyophilized in a subsequent step.

The first step can be advantageously replaced with an operation of simple freezing of the plant tissues (for example at −20° C. or even at −180° C. in liquid nitrogen), followed by an aqueous extraction repeating the second and third steps described above.

The cold-temperature treatment allows the enzymatic activities to be frozen, and the sterilizing filtration avoids the degradation of the active agents by environmental microorganisms. Finally, the water vehicle is compatible with the ex vivo receptors and facilitates the cosmetic formulations.

It is known that plant extracts contain, other than proteases which can harm the quality of the extract, oxidases which are responsible, inter alia, for the oxidation of said extracts. In point of fact, such an oxidation imparts to the extracts a dark brown color and an acrid odor, thus rendering them unsuitable for use in cosmetics. Similarly, a lactase whose molecular weight is greater than 100,000 daltons is known, in particular.

Thus, the extract obtained can advantageously be fractionated by any known fractionation method for removing oxidases and in particular polyphenol oxidase. For example, the extract of the invention can be filtered through a dialysis membrane in order to remove the molecules with a molecular weight of greater than 100,000 daltons. It is also possible to subject the extract to a fractionation by selective precipitations.

Other technique are available to protect against oxidation phenomena. In particular, the extract can also be stabilized. Any known stabilization method can be used according to the invention. For example, the extract of the invention can be stabilized by bubbling nitrogen therethrough in order to remove the dissolved oxygen, or alternatively by adding cysteine and/or sulfur derivatives thereto to a final concentration ranging from 0.5 g/l to 10 g/l and preferably from 1 g/l to 2.5 g/l.

It will of course be appreciated that the extract according to the invention can be fractionated and stabilized.

The extract can itself constitute the active principle of the compositions of the invention.

One embodiment of a preparation of an extract which can be employed according to the invention is given in the examples which follow.

The amount of extract which can be used according to the invention obviously depends on the desired effect and can thus vary over a wide range.

In order to provide an order of magnitude, an extract as described above is advantageously employed in an amount representing from 0.01% to 20% of the total weight of the composition and preferably in an amount representing from 0.1% to 5% relative to the total weight of the composition.

The undifferentiated plant cells according to the invention can originate from any known plant species.

In this respect, particularly exemplary are the genera Salvia, Coleus, Rosmarinus, Ginkgo, Cannabis, Colchicum, Gloriosa, Asparagus, Glycine, Medicago, Mungo, Erythrina, Oenothera, Papaver, Atropa, Datura, Solanum, Borago, Reseda, Amsonia, Catharantus, Pilocarpus, Digitalis, Coffea, Theobroma, Jasminum, Capsicum and Iris.

Undifferentiated plant cells originating from plants of the genus Ginkgo, Theobroma, Salvia or Datura are particularly preferred according to the invention.

It will also be appreciated that the extracts of undifferentiated plant cells according to the invention can originate from mixtures of undifferentiated plant cells obtained from different plant genera and/or obtained from different plant material.

This invention thus features body hygiene compositions, comprising, formulated into a physiologically and cosmetically acceptable medium (vehicle, diluent or carrier), at least one extract of undifferentiated plant cells, with the exception of cells from the genus Bellis. The body hygiene composition is advantageously a deodorant composition.

The compositions of the invention can be a cosmetic or dermatological composition. Consistent herewith, the composition is preferably a cosmetic composition, particularly for topical application.

The present invention also features a cosmetic treatment regime/regimen for the skin which is intended to inhibit odors, comprising topically applying a cosmetic composition containing at least one extract of undifferentiated plant cells, with the exception of cells from the genus Bellis, onto the skin, the hair and/or mucous membranes.

The cosmetic regime/regimen of the invention can be carried out, in particular, by topically applying the cosmetic compositions as described above, according to the usual techniques for administration of these compositions. For example, application of creams, gels, sera, ointments, lotions, milks, cream/gels, shampoos or antisun/sunscreen compositions onto the skin.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Preparation of Undifferentiated Plant Cells from *Salvia Miltiorrhiza* (Sage)

After removing the leaves, the plant was decontaminated with saturated sodium or calcium hypochlorite solutions at a concentration of 290 g/l, at room temperature (25° C.) for a period of between 1 and 5 minutes. The tissues were rinsed with sterile distilled water and then placed in a dilute ethanol solution. They were subjected to 3 washes with sterile distilled water at the end of decontamination.

The explants were then chopped up under sterile conditions under a laminar-flow fume cupboard and were then placed in petri dishes on Murashige-Skoog medium. The primary calli appeared within 2 to 5 weeks. The primary calli were then subcultured on fresh agar prepared with the same culture medium. As the subculturing continued, the cells stabilized (appearance, color, etc.) and could be transferred in liquid medium in order, optionally, to be cultivated industrially in a fermenter.

| Murashige-Skoog medium: | |
| --- | --- |
| Skoog macroelements | 100.00 ml |
| Skoog microelements | 1.00 ml |
| Skoog vitamins | 2.00 ml |
| Iron/EDTA | 10.00 ml |
| $10^{-4}$M 2,4-dichlorophenoxyacetic acid | 10.00 ml |
| $10^{-4}$M kinetin | 0.60 ml |
| Sucrose | 30.00 g |
| Agar | 8.00 g |
| Distilled water | qs 1 liter |
| pH before sterilization | 5.8 UpH |

Sterilization at 115 or 121° C. for 20 to 40 minutes

| Skoog macroelements in mg/l: | |
| --- | --- |
| $KNO_3$ | 1900 |
| $NH_4NO_3$ | 1650 |
| $MgSO_4 \cdot 7 H_2O$ | 370 |
| $CaCl_2 \cdot 2 H_2O$ | 440 |
| $KH_2PO_4$ | 170 |
| Skoog microelements in mg/l: | |
| $CuSO_4 \cdot 5 H_2O$ | 0.025 |
| $MnSO_4 \cdot 1 H_2O$ | 16.90 |
| KI | 0.83 |
| $NaMoO_4 \cdot 2 H_2O$ | 0.25 |
| $ZnSO_4 \cdot 7 H_2O$ | 10.60 |
| $H_3BO_3$ | 6.20 |
| $CoCl_2 \cdot 6 H_2O$ | 0.025 |
| Skoog vitamins in mg/l: | |
| Myoinositol | 100.00 |
| Nicotinic acid | 0.50 |
| Pyridoxine | 0.50 |
| Thiamine | 0.10 |
| Iron/EDTA: | |
| $FeSO_4 \cdot 7 H_2O$ | 27.8 |
| $Na_2$ EDTA | 37.3 |

EXAMPLE 2

Preparation of the Extracts 10 grams of stabilized cells obtained in Example 1 were recovered by filtration on a 50 to 100 μm gauze depending on the size of the cell aggregates.

The cells were placed at −20° C. under slow freezing, which promotes the formation of large intracellular crystals allowing the cells to be broken by cryogenic grinding (freezer).

The thawed cells were placed at 4° C. and then ground more finely with a Potter machine in 10 ml of distilled water. Two grindings were thus carried out.

The materials in suspension were removed by centrifugation at 8000×G for 10 minutes at 4° C.

The supernatant was prefiltered on Whatman GF/F paper 7 cm in diameter, followed by filtration through a 0.22 μm to remove the fine particles remaining in suspension.

About 12 ml directly usable extract were obtained.

The products thus obtained were lyophilized. About 1 gram of extract (dry weight) was obtained after lyophilization.

0.1 gram of each extract was placed in a pill box containing 1 ml of fresh sweat.

The fresh sweat was recovered by means of a leakproof clothing placed on each sweat donor before the donor enters a sauna.

EXAMPLE 3

Olfactory Evaluation of the Inhibitory Effect of Extracts of Undifferentiated Plant Cells Prepared According to Example 1

The evaluation was carried out by four trained testers.

The evaluation of the odor of each sample was carried out randomly and graded.

The two evaluation criteria and the gradings were as follows:

| Overall intensity: | | | | | |
| --- | --- | --- | --- | --- | --- |
| Grade | 0 | 1 | 2 | 3 | 4 |
| Intensity | zero | slight | moderate | strong | very strong |

| Hedonic assessment: | |
| --- | --- |
| Grade | |
| 0 | very pleasant |
| 1 | pleasant |
| 2 | mildly pleasant |
| 3 | neutral |
| 4 | slightly unpleasant |
| 5 | unpleasant |
| 6 | very unpleasant |

A second evaluation could be carried out 6 hours after the first.

Materials and Method

A pool of mixed human underarm sweat obtained from 4 to 6 individuals was produced by thermal stimulation (sauna at about 80° C. and 20–30% relative humidity for 2 hours). The fresh sweat was recovered by means of a leakproof clothing placed on each sweat donor before the donor entered the sauna.

100 mg of extract were then introduced into a 30 ml white glass pill box (Ø of the aperture 25 mm) with a stopper protected on the inside by aluminum foil.

1 ml of fresh sweat was introduced into each flask.

The assembly was shaken moderately.

The pH was evaluated using reactive strips.

The flasks were stoppered then incubated at 37° C.

The olfactory evaluation was carried out after incubation for 18 hours.

The intensity and unpleasantness of the odor were positioned relative to a sample of sweat without addition of active agent which was fully identified, and which was evaluated first and re-evaluated as many times as necessary. An unidentified efficacy control containing 0.8 mg of triclosan (bacteriostatic agent) as well as a sweat control without active agent, but unidentified, were added to the series of samples to be evaluated.

Evaluation

The flasks were removed after incubation for 18 hours in an incubator thermostatically set at 37° C. They were opened and placed in a ventilated fume cupboard for a minimum of 10 minutes before being evaluated.

Results

The averages of the grades attributed by each of the evaluators was calculated for each extract. The results are expressed as a percentage variation of the intensity and of each hedonic grade relative to the control free of active agent. The higher the percentage variations obtained, the greater the efficacy of the extract.

| Genus | % intensity inhibition | % hedonic variation |
|---|---|---|
| Ginkgo cultivated in light | 23.1 | 28.3 |
| Ginkgo cultivated in darkness | 23.1 | 37.0 |
| Salvia cultivated in darkness | 26.9 | 14.0 |
| Cacao cultivated in darkness | 37.9 | 15.6 |
| Datura cultivated in light | 20.7 | 13.3 |

EXAMPLE 4

The following are specific examples of formulations according to the invention.

These compositions were formulated by simple mixing of the various constituents thereof.

| Composition 1: deodorant lotion | |
|---|---|
| 2-Ethylhexyl palmitate | 35.00 g |
| Cyclopentadimethylsiloxane | 6.60 g |
| Butylene glycol | 5.00 g |
| Extract of sage | 2.50 g |
| Preservatives | qs |
| Demineralized water | qs 100.00 g |

| Composition 2: deodorant cream | |
|---|---|
| Mixture of cetylstearyl alcohol/30 EO cetylstearyl alcohol | 7.00 g |
| Glyceryl mono/distearate | 2.00 g |
| Liquid petroleum jelly | 15.00 g |
| Glycerol | 20.00 g |
| Extract of sage | 5.00 g |
| Fragrance, preservative | qs |
| Demineralized water | qs 100.00 g |

| Composition 3: deodorant milk | |
|---|---|
| 2-Ethylhexyl palmitate | 35.00 g |
| Glycerol | 2.00 g |
| Extract of sage | 3.00 g |
| Crosslinked acrylic acid/C10–C30 alkyl acrylate copolymer | 0.10 g |
| Triethanolamine | 0.10 g |
| Amino acids from wheat in aqueous solution | 1.00 g |
| Preservatives qs | |
| Demineralized water | qs 100.00 g |

| Composition 4: deodorant gel | |
|---|---|
| Sodium behenoyl lactylate | 10.00 g |
| Glycerol | 2.00 g |
| Extract of sage | 2.50 g |
| Zinc ricinoleate | 1.00 g |
| Stearic acid | 8.40 g |
| Sodium hydroxide | 1.20 g |
| Fragrance, dyes, preservatives | qs |
| Demineralized water | qs 100.00 g |

| Composition 5: water-in-silicone emulsion | |
|---|---|
| Silicone DC 245 Fluid (Dow Corning) | 6.60 g |
| Silicone DC 5225 C (Dow Corning) | 9.40 g |
| Ethyl alcohol | 11.00 g |
| Extract of sage | 3.00 g |
| Propylene glycol | 37.00 g |
| Fragrance, preservatives | qs |
| Demineralized water | qs 100.00 g |

| Composition 6: alcoholic deodorant stick | |
|---|---|
| Stearic acid | 7.00 g |
| Sodium hydroxide | 1.08 g |
| Isopropyl myristate | 5.00 g |
| Extract of sage | 2.50 g |
| Ethyl alcohol | 60.80 g |
| Propylene glycol | 20.50 g |
| Fragrance qs | |
| Demineralized water | qs 100.00 g |

| Composition 7: anhydrous antiperspirant stick | |
|---|---|
| Stearyl alcohol | 22.00 g |
| Hydrogenated castor oil | 5.00 g |
| Isopropyl palmitate | 12.50 g |
| Anhydrous aluminum hexachloride | 20.00 g |
| Extract of sage | 0.50 g |
| Cyclopentadimethylsiloxane | 35.00 g |
| Talc | 5.00 g |

While the invention has been described in terms of various specific and/or preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inhibiting disagreeable/objectionable body odors, comprising treating a situs thereof with a composition comprising at least one aqueous, alcoholic or aqueous/alcoholic extract of undifferentiated plant cells, other than cells of the genus Bellis, and a physiologically/cosmetically acceptable vehicle, diluent or carrier therefor, wherein said extract is effective for inhibiting said disagreeable/objectionable body odors, and wherein said composition does not contain an anti-perspirant.

2. A regime/regimen for inhibiting disagreeable/objectionable body odor, comprising administering to an individual subject in need of such treatment, a composition comprising at least one aqueous, alcoholic or aqueous/alcoholic extract of undifferentiated plant cells, other than cells of the genus Bellis, and a physiologically/cosmetically acceptable vehicle, diluent or carrier therefor, wherein said extract is effective for inhibiting said disagreeable/objectionable body odor, and wherein said composition does not contain an anti-perspirant.

3. A regime/regimen for inhibiting disagreeable/objectionable body odor, comprising topically applying onto the skin, hair and/or mucous membranes of an individual subject in need of such treatment, a topically applicable composition comprising an effective body odor-inhibiting amount of at least one aqueous, alcoholic or aqueous/alcoholic extract of undifferentiated plant cells, other than cells of the genus Bellis, and a topically applicable, physiologically/cosmetically acceptable vehicle, diluent or carrier therefor, wherein said composition does not contain an anti-perspirant.

4. A regime/regimen for inhibiting disagreeable/objectionable body sweat odors, comprising administering to an individual subject in need of such treatment, a composition comprising an amount of at least one aqueous, alcoholic or aqueous/alcoholic extract of undifferentiated plant cells, other than cells of the genus Bellis, effective to inhibit said body sweat odors, and a physiologically/cosmetically acceptable vehicle, diluent or carrier therefor, and wherein said composition does not contain an anti-perspirant.

5. The regime/regimen according to claim 4, comprising inhibiting disagreeable/objectionable human sweat odors.

6. The regime/regimen for inhibiting disagreeable/objectionable body odor according to claim 2, wherein said undifferentiated plant cells have been separated from whole plant, or from a plant part.

7. The regime/regimen for inhibiting disagreeable/objectionable body odor according to claim 6, wherein said undifferentiated plant cells have been separated from leaves, stalks, flowers, petals, roots, fruit, seed or anthers of said plant or plant part.

8. The regime/regimen for inhibiting disagreeable/objectionable body odor according to claim 7, wherein said undifferentiated plant cells have been separated from leaves of said plant or plant part.

9. The regime/regimen for inhibiting disagreeable/objectionable body odor according to claim 6, wherein said undifferentiated plant cells have been separated from a plant cultivated in vivo or obtained via in vitro cultivation.

10. The regime/regimen for inhibiting disagreeable/objectionable body odor according to claim 9, wherein said undifferentiated plant cells have been obtained via in vitro cultivation.

11. The regime/regimen for inhibiting disagreeable/objectionable body odor according to claim 2, wherein said at least one extract of undifferentiated plant cells comprises an aqueous or aqueous/alcoholic extract.

12. The regime/regimen for inhibiting disagreeable/objectionable body odor according to claim 2, wherein said undifferentiated plant cells have been separated from a plant of the genus Salvia, Coleus, Rosmarinus, Ginkgo, Cannabis, Colchicum, Gloriosa, Asparagus, Glycine, Medicago, Mungo, Erythrina, Oenothera, Papaver, Atropa, Datura, Solanum, Borago, Reseda, Amsonia, Catharantus, Pilocarpus, Digitalis, Coffea, Theobroma, Jasminum, Capsicum or Iris.

13. The regime/regimen for inhibiting disagreeable/objectionable body odor according to claim 12, wherein said undifferentiated plant cells have been separated from a plant of the genus Ginkgo, Theobroma, Salvia or Datura.

14. The regime/regimen for inhibiting disagreeable/objectionable body odor according to claim 2, wherein said at least one extract of undifferentiated plant cells is reduced in oxidase values.

15. A method for inhibiting disagreeable/objectionable body odor, comprising topically applying onto the skin, hair and/or mucous membranes of an individual subject in need of such treatment, a topically applicable composition comprising an effective body odor-inhibiting amount of at least one aqueous, alcoholic or aqueous/alcoholic extract of undifferentiated plant cells, other than cells of the genus Bellis, and a topically applicable, physiologically/cosmetically acceptable vehicle, diluent or carrier therefor, wherein said composition does not contain an antiperspirant, said composition being formulated as a cream, gel, serum, ointment, lotion, milk, cream/gel, shampoo or sunscreen.

* * * * *